United States Patent [19]

Pierantozzi

[11] Patent Number: 4,521,540

[45] Date of Patent: Jun. 4, 1985

[54] PROCESS FOR PRODUCING DIMETHYL ETHER FORM SYNTHESIS GAS

[75] Inventor: Ronald Pierantozzi, Macungie, Pa.

[73] Assignee: Air Products and Chemicals, Inc., Allentown, Pa.

[21] Appl. No.: 592,324

[22] Filed: Mar. 22, 1984

[51] Int. Cl.$^3$ .............................................. C07C 27/06
[52] U.S. Cl. .................................... 518/717; 502/161
[58] Field of Search ........................................ 518/717

[56] References Cited

U.S. PATENT DOCUMENTS

| | | | |
|---|---|---|---|
| 3,894,102 | 7/1975 | Chang et al. | 260/668 |
| 3,941,819 | 3/1976 | Vannice et al. | 260/449 |
| 4,098,809 | 7/1978 | Pagnal | 260/449 |
| 4,154,751 | 5/1979 | McVicker et al. | 260/449.6 |
| 4,177,167 | 12/1979 | Manara et al. | 252/455 |
| 4,328,129 | 5/1982 | Huang | 252/465 |

FOREIGN PATENT DOCUMENTS 2093365  9/1982  United Kingdom .

OTHER PUBLICATIONS

React. Kinet. Catal. Lett., vol. 20, Nos. 1-2, 175-180(1982), Light Olefin Production from $CO/H_2$ Over Silica Supported Fe/Mn/K Catalysts Derived From a Bimetallic Carbonyl Anion, $[Fe_2Mn(CO)_{12}]$.

*Primary Examiner*—Howard T. Mars
*Attorney, Agent, or Firm*—Russell L. Brewer; E. Eugene Innis; James C. Simmons

[57] ABSTRACT

This invention pertains to a Fischer Tropsch process for converting synthesis gas to an oxygenated hydrocarbon with particular emphasis on dimethyl ether. Synthesis gas comprising carbon monoxide and hydrogen are converted to dimethyl ether by carrying out the reaction in the presence of an alkali metal-manganese-iron carbonyl cluster incorporated onto a zirconia-alumina support.

5 Claims, No Drawings

PROCESS FOR PRODUCING DIMETHYL ETHER FORM SYNTHESIS GAS

REFERENCE TO GOVERNMENT CONTRACT

This invention was made in the performance of a research and development contract with the U.S. Department of Energy, the contract number being DE-AC22-80PC30021.

BACKGROUND OF THE INVENTION

The Fischer Tropsch process for converting synthesis gas comprising carbon monoxide and hydrogen into a variety of hydrocarbons and oxygenated hydrocarbons has been investigated for some time, and a variety of products have been produced by this technique. Examples of products include $C_2$ to $C_6$ olefins, lights, e.g. $C_1$-$C_2$ paraffins, $C_6$ to $C_{10}$ hydrocarbons e.g. gasoline and kerosene, as well as oxygenated hydrocarbons, such as, methanol, dimethyl ether, various esters, acids and alcohols. Selectivity to a particular product is influenced substantially by the process conditions utilized, e.g. in terms of temperature and pressure as well as the catalyst utilized in the reaction.

U.S. Pat. No. 4,328,129 discloses a Fischer Tropsch process for producing dimethyl ether and methanol in high selectivity by contacting a gaseous mixture of carbon monoxide and hydrogen with a rhodium-molybdenum catalyst, the condition being monitored to favor production of these two materials. In the background portion of the patent, it is indicated that U.S. Pat. No. 3,941,819 discloses the production of dimethyl ether over a calalyst system consisting of platinum supported on alumina.

U.S. Pat. No. 4,098,809 discloses a process for producing dimethyl ether in a Fischer Tropsch process utilizing a methanol synthesis catalyst, such as a copper base or chromium-zinc base catalyst.

U.S. Pat. No. 3,894,102 discloses a process for converting synthesis gas to dimethyl ether and then subsequently to a high octane gasoline. The first stage of the process involves reacting carbon monoxide with hydrogen in the presence of a mixed methanol synthesis and acidic dehydration catalyst. Temperatures from about 300°–700° F., elevated pressures, e.g. up to about 10,000 psig, and space velocities of at least 500 GHSV are used in the first stage to produce dimethyl ether.

U.S. Pat. No. 4,177,167 discloses a process for producing dimethyl ether by the catalyst reaction of carbon monoxide and hydrogen utilizing a mixture of oxides or salts of metals such as aluminum, chromium, lanthanum, manganese, copper or zinc as a catalyst.

U.S. Pat. No. 4,154,751 discloses a series of supported potassium or rubidium-Group 8 metal cluster catalysts for producing a variety of components in a Fischer Tropsch process. Examples of precursor bimetallic cluster complexes include potassium-iron carbonyl compounds, potassium-nickel carbonyl compounds and potassium-platinum carbonyl compounds though the corresponding rubidium complexes are also shown. These catalysts produce predominantly hydrocarbon products with little or no oxygenate selectivity.

Great Britain No. 2,093,365, describes a catalyst consisting of copper, zinc and alumina which is effective for the conversion of synthesis gas to dimethyl ether.

SUMMARY OF THE INVENTION

This invention pertains to an improved catalytic process Fischer Tropsch process for converting synthesis gas comprising carbon monoxide and hydrogen to dimethyl ether. The improvement in the Fischer Tropsch Process comprises effecting the reaction in the presence of an alkali metal-manganese-iron carbonyl cluster incorporated onto a zirconia-alumina support.

Some of the advantages associated with the invention are:
dimethyl ether is formed in high selectivity while methane production is low, and
dimethyl ether is formed at significant rates.

DETAILED DESCRIPTION OF THE INVENTION

As in the prior art conversion of carbon monoxide and hydrogen to dimethyl ether via the Fischer Tropsch Process, a mixture of a carbon monoxide and hydrogen is effected by contacting the mixture with a catalyst under gas phase conditions for a time and temperature sufficient to effect conversion to the product. Typically, the ratio of carbon monoxide to hydrogen, on a molar basis, is from 0.5 to 2 moles carbon monoxide per mole hydrogen.

The temperatures and pressures utilized for carrying out the process are conventional and adjusted within the reaction zone to favor dimethyl ether production as desired. Generally temperatures used in the reaction are within a range from 200° to 400° C., and preferably 225° to 270° C. and pressures are within a range from 100 to 1000 psig, and preferably 300 to 600 psig.

Unlike the prior art the catalyst utilized in the process is a metal carbonyl cluster. $K[Fe_2Mn(CO)_{12}]$ or other alkali metal salt, e.g., potassium, sodium, lithium, etc., of the anionic $[Fe_2Mn(CO)_{12}]^-$ cluster. An example of such a cluster is represented by the formula:

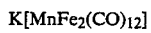

$K[MnFe_2(CO)_{12}]$

The carrier substrate for the alkali metal salt of the iron-manganese carbonyl cluster is a high surface area material and can be prepared by reacting a solution of zirconium alkoxide or other alkoxides such as titanium with alumina. The support generally comprises a mixture of zirconia and alumina with 5–30 wt % zirconia. The presence of zirconia in combination with alumina and the combination with the carbon cluster enhances conversion to dimethyl ether, whereas a support comprising essentially alumina, e.g. greater than 95% by weight of the support, favors the production of hydrocarbons.

The catalyst comprising the alkali metal-manganese-iron carbonyl complex supported on a zirconia-alumina support may be prepared in conventional manner which usually involves reacting the metal carbonyl salt with the support. Generally the reaction is effected by suspending the metal carbonyl complex in a liquid carrier, such as diethyl ether, and contacting the support with the suspension. After contact, the sample is dried in vacuum. No further catalyst pretreatment is required. The level of metal carbonyl cluster present on the support is preferably within a range from about 0.5 to 5% by weight.

The following examples are provided to illustrate various embodiments of the invention.

EXAMPLE 1

Support Preparation

A zirconia-alumina g support was prepared by mixing 300 g of $Al_2O_3$ previously treated at 200° C. under vacuum with a solution of zirconium propoxide $[Zr(OPr)_4]$ (OPr representing the propoxide radical) so that the $Al_2O_3$ surface was thoroughly wet. The solution contained 63.86 g (60.82 ml) of $Zr(OPr)_4$ in 200 ml dry hexane. After mixing, the resulting wet solid was dried under vacuum. The loading level of zirconium was 9.07% by weight of the support.

EXAMPLE 2

Catalyst Preparation

A 0.63 g sample of $K[MnFe_2(CO)_{12}]$ was prepared in accordance with a conventional procedure set forth in Ruff, *Inorganic Chemistry*, 7(9) 1818 (1968) and dissolved in 200 ml of dry diethyl ether. The solution was gently heated to dissolve the cluster and when dissolved small aliquots were added to 12 g of the support from Example 1. The aliquot was sized so only that amount necessary to wet the support was used. After each addition of the aliquot, the support was dried. The process was repeated until all of the solution was used. The final catalyst loading contained 0.92% Fe and 0.51% Mn.

EXAMPLE 3

A series of runs were carried out to determine the effectiveness of a variety of catalyst systems in converting synthesis gas to dimethyl ether. Such experiments were carried out in a gas-phase reactor system consisting of a stainless steel tube of 9 inches in length and having an internal diameter of ½ inch. The reactor then was packed with various catalyst materials to provide a bed depth of about 7 inches within the reactor. The feed gases of hydrogen and carbon monoxide were introduced into the reactor and the reaction zone after preheating to 250° C. The reaction products were removed from the bottom of the reactor and analyzed by gas chromotography.

Table 1 provides a description of the various process conditions utilized with numerous catalyst systems, and Table 2 provides a corresponding analysis of the product mix. A more detailed explanation of specific points regarding the example may allow the table and are numbered accordingly. The catalysts were prepared in accordance with general techniques, including the techniques set forth in Examples 1 and 2. More particularly, some of the variables within Table 1 include: catalyst, which represents the active metal component; the support, which represents the general type of support, e.g. $Zr/Al_2O_3$, $Al_2O_3$ etc., mole ratio of $CO/H_2$ in the feed, reaction temperature and pressure in kilo Pascal, gas hourly space velocity (GHSV) and time on stream. MeOH, EtOH and PrOH refers to methanol, ethanol and propanol respectively. Runs 1–5 used the Example 2 catalyst.

TABLE 1

| RUN | CATALYST | SUPPORT | MOLE RATIO $CO/H_2$ | REACTION T °C. | P kPa | GHSV $m^3/l \cdot h$ | TIME ON STREAM HOURS |
| --- | --- | --- | --- | --- | --- | --- | --- |
| 1 | $K[MnFe_2(CO)_{12}]$ | Ex 1 | 1 | 203 | 2100 | 598 | 13 |
| 2 | " | Ex 1 | 1 | 251 | 2100 | 299 | 45 |
| 3 | " | Ex 1 | 1 | 248 | 2100 | 299 | 60 |
| 4 | " | Ex 1 | 0.5 | 247 | 2100 | 612 | 132 |
| 5 | " | Ex 1 | 1 | 280 | 2100 | 299 | 158 |
| 6 | " | $Al_2O_3$ | 1 | 265 | 2100 | 295 | 5 |
| 7 | " | MgO | 1 | 262 | 2100 | 596 | 96 |
| 8 | " | MgO | 0.5 | 277 | 2100 | 592 | 149 |
| 9 | $Co_2(CO)_8$ | Ex 1 | 2 | 242 | 2100 | 607 | 36 |
| 10 | $Fe_3(CO)_{12}$ | Ex 1 | 1 | 270 | 2100 | 201 | 169 |

TABLE 2

| | | Product Distribution (wt %) | | | | | | | |
| --- | --- | --- | --- | --- | --- | --- | --- | --- | --- |
| RUN | CO CONV. | $C_1$ | $C_2$–$C_4$ | $C_5$–$C_{11}$ | $C_{12}+$ | DME | MeOH | EtOH | PrOH |
| 1 | 19.9 | 12.8 | 20.6 | 10.6 | 0 | 14.9 | 31.2 | 3.4 | 6.6 |
| 2 | 48.0 | 7.9 | 6.5 | 3.9 | 0 | 46.8 | 19.7 | 0.6 | 13.0 |
| 3 | 47.8 | 19.5 | 20.4 | 4.7 | 0 | 41.3 | 16.4 | 2.7 | 0 |
| 4 | 34.7 | 18.0 | 18.9 | 0 | 0 | 42.8 | 20.4 | 0 | 0 |
| 5 | 58.4 | 6.9 | 13.3 | 0.7 | 0 | 65.7 | 13.5 | 0 | 0 |
| 6 | 64.5 | 18.3 | 37.3 | 14.7 | 11.0 | 0.8 | 6.9 | 9.8 | 5.9 |
| 7 | 15.6 | 58.6 | 29.6 | 11.8 | 0 | 0 | 0 | 0 | 0 |
| 8 | 9.0 | 54.6 | 22.6 | 0 | 0 | 0 | 11.2 | 7.3 | 0 |
| 9 | 33.3 | 24.4 | 24.4 | 37.0 | 13.2 | 0 | 0 | 0.80 | 0.62 |
| 10 | 3.2 | 6.7 | 50.4 | 34.9 | 0 | 1.16 | 1.92 | 0 | 4.77 |

Runs 1–5 show good selectivity of DME production since there is very little ethanol and propanol production. Further, since there is little hydrocarbon production, this shows the catalyst and support are well suited to produce oxygenated derivatives from synthesis gas. The conversion observed in Run 1 is low due to process conditions. Runs 6–8 show that when the support was altered having only the $K[MnFe_2(CO)_{12}]$ active component, the percentage of oxygenates decreased substantially even though there was good conversion, based upon CO. Runs 9 and 10 show the importance of the active metal-carbonyl cluster component for achieving high selectivity to oxygenates.

Runs 6–8—The cluster $K[MnFe_2(CO)_{12}]$ was supported on $Al_2O_3$ and MgO in a manner analogous to that described in Example 2 after pretreating the supports at 200° C. in vacuum. The catalyst testing results are summarized in Table 1, Runs 6, 7 and 8.

The MgO supported catalyst contained 1.32 wt % Fe and 0.92 wt % Mn. The $Al_2O_3$ supported catalyst contained 1.70 wt % Fe and 0.77 wt % Mn.

Runs 9 and 10—The [Co$_2$(CO)$_8$] was added to the Zr(OPr)$_4$/Al$_2$O$_3$ support, prepared in Ex 1 by a method analogous to that described in Ex 1.

The catalyst contained 1.99 wt % Co. The catalyst testing results are shown in Run 9. The Fe$_3$(CO)$_{12}$ was incorporated in the same way as the Co$_2$(CO)$_8$. The catalyst contained 0.83% Fe.

What is claimed is:

1. In a Fischer Tropsch Process for converting synthesis gas comprising carbon monoxide and hydrogen to oxygenated hydrocarbons, said conversion being effected by reacting carbon monoxide and hydrogen in the gas phase over a metal carbonyl cluster catalyst, for a time and at a temperature sufficient to form said oxygenated hydrocarbon, the improvement for selectively forming dimethyl ethyl which comprises utilizing an alkali metal salt of a manganese-iron carbonyl cluster supported on a zirconia-alumina support.

2. The process of claim 1 wherein the percent zirconia in said support is from 5 to 30% by weight.

3. The process of claim 2 wherein the support is present in an amount of from 50 to 99% by weight of the catalyst.

4. The process of claim 3 wherein said metal carbonyl cluster is a potassium salt of a manganese-iron carbonyl cluster.

5. The process of claim 4 wherein said metal carbonyl catalyst composition is represented by the formula:

K[MnFe$_2$(CO)$_{12}$]/ZrAl$_2$O$_3$.